United States Patent
Xing (10) Patent No.: US 11,597,741 B2
(45) Date of Patent: Mar. 7, 2023

(54) PROCESSES AND MATERIALS FOR THE SYNTHESIS OF SUGAR ESTERS FOUND IN NATURAL TOBACCO

(71) Applicant: Myst Labs Inc., San Jose, CA (US)

(72) Inventor: Chenyue Xing, San Mateo, CA (US)

(73) Assignee: Myst Labs Inc., San Jose, CA (US)

( * ) Notice: Subject to any disclaimer, the term of this patent is extended or adjusted under 35 U.S.C. 154(b) by 0 days.

(21) Appl. No.: 17/401,009

(22) Filed: Aug. 12, 2021

(65) Prior Publication Data

US 2022/0048938 A1    Feb. 17, 2022

Related U.S. Application Data (60) Provisional application No. 63/065,038, filed on Aug. 13, 2020.

(51) Int. Cl.
*C07H 13/04* (2006.01)
*C07H 1/00* (2006.01)

(52) U.S. Cl.
CPC .............. *C07H 13/04* (2013.01); *C07H 1/00* (2013.01)

(58) Field of Classification Search
None
See application file for complete search history.

(56) References Cited

U.S. PATENT DOCUMENTS

| | | |
|---|---|---|
| 3,053,677 A | 9/1962 | Touey et al. |
| 4,657,690 A | 4/1987 | Grollier |
| 4,997,817 A | 3/1991 | Pettit |
| 5,041,541 A | 8/1991 | Mazur et al. |

FOREIGN PATENT DOCUMENTS

| | | |
|---|---|---|
| WO | 2019236772 A1 | 12/2019 |

OTHER PUBLICATIONS

Shaw et al., Biotechnology and Bioengineering, vol. XXIX, pp. 648-651 1987. (Year: 1987).*
Shaw et al., "Preparation of Various Glucose Esters via Lipase-Catalyzed Hydrolysisof Glucose Pentaacetate," Biotechnology and Bioengineering, vol. XXIX (1986).
Search Report and Written Opinion issued in International Application No. PCT/US21/45662 dated Nov. 23, 2021.

* cited by examiner

*Primary Examiner* — Traviss C McIntosh, III
(74) *Attorney, Agent, or Firm* — Brian J. Colandreo; Michael T. Abramson; Holland & Knight LLP (57) ABSTRACT

A process and materials method for making a glucose tetraester may include reacting glucose with a carboxylic acid to create a glucose pentaester. The glucose pentaester was reacted with a basic reagent to create a glucose tetraester. Glucose was reacted with a carboxylic acid anhydride in the presence of 4-dimethylaminopyridine to create a glucose pentaester product. The glucose pentaester reaction product was separated. The glucose pentaester reaction product was reacted with a basic reagent, wherein the reaction steps may take place at a temperature of about 0° C. to about 60° C. and about ambient pressure, wherein the ratio of the carboxylic acid to the glucose was from about 5:1 to about 50:1, and wherein the ratio of the glucose pentaester to the basic reagent was from about 1:50 to about 1:150.

20 Claims, 10 Drawing Sheets

PROCESSES AND MATERIALS FOR THE SYNTHESIS OF SUGAR ESTERS FOUND IN NATURAL TOBACCO

RELATED CASES

This application claims the benefit of U.S. Provisional Application No. 63/065,038, filed on 13 Aug. 2020, the contents of which are all incorporated by reference.

BACKGROUND

Typically, some processes may attempt to manufacture tobacco material that enriches sugar esters (or other compounds), which is focusing on raising the concentration of such compounds during the drying of the tobacco leaf. Generally, some sugar ester synthesis processes may require enzyme catalysis. Such enzyme catalysis processes may be sensitive to environmental parameters. Without careful control of reaction conditions, the enzyme may be impacted and lose its activity. Such reactions typically have lower than, e.g., 80% purity.

BRIEF SUMMARY OF DISCLOSURE

In one example implementation, a process for making a glucose tetraester may include but is not limited to reacting glucose with a carboxylic acid or a carboxylic acid anhydride to create a glucose pentaester. The glucose pentaester was reacted with a basic reagent to create a glucose tetraester.

One or more of the following example features may be included. The reactions are not enzyme catalyzed. The reaction of glucose with the carboxylic acid is performed at a temperature of about 0° C. to about 60° C. The reaction of the glucose pentaester with the basic reagent is performed at a temperature of about 0° C. to about 60° C. The glucose tetraester is glucose tetramethylvalerate. The glucose tetraester is glucose tetrapropionate. The glucose tetraester is glucose tetravalerate. The glucose is α-D-glucose. The reaction of glucose with the carboxylic acid takes place in the presence of 4-dimethylaminopyridine. The reaction of glucose with the carboxylic acid is performed at about ambient pressure. The basic reagent is ammonia. A ratio of the carboxylic acid to glucose is from about 5:1 to about 50:1. A ratio of the carboxylic acid to glucose is from about 10:1 to about 40:1. A ratio of the glucose pentaester to the basic reagent is from about 1:50 to about 1:150. The glucose pentaester product includes one of glucose pentamethylvalerate, glucose pentaproprionate, and glucose pentavalerate.

In another example implementation, a process for making a glucose tetraester may include but is not limited to reacting glucose with a carboxylic acid anhydride in the presence of 4-dimethylaminopyridine to create a glucose pentaester product. The glucose pentaester reaction product was separated. The glucose pentaester reaction product was reacted with a basic reagent, wherein the reaction steps may take place at a temperature of about 0° C. to about 60° C. and about ambient pressure, wherein the ratio of the carboxylic acid to the glucose was from about 5:1 to about 50:1, and wherein the ratio of the glucose pentaester to the basic reagent was from about 1:50 to about 1:150.

One or more of the following example features may be included. The glucose tetraester is glucose tetramethylvalerate. The glucose tetraester is glucose tetrapropionate. The glucose tetraester is glucose tetravalerate. The basic reagent is ammonia. The reactions are not enzyme catalyzed. The glucose tetraester is glucose tetravalerate. The glucose is α-D-glucose. The basic reagent is ammonia. A ratio of the carboxylic acid to glucose is from about 10:1 to about 40:1. The glucose pentaester product includes one of glucose pentamethylvalerate, glucose pentaproprionate, and glucose pentavalerate.

The details of one or more example implementations are set forth in the accompanying drawings and the description below. Other possible example features and/or possible example advantages will become apparent from the description, the drawings, and the claims. Some implementations may not have those possible example features and/or possible example advantages, and such possible example features and/or possible example advantages may not necessarily be required of some implementations.

BRIEF DESCRIPTION OF THE DRAWINGS

Like reference symbols in the various drawings may indicate like elements.

DETAILED DESCRIPTION

Electronic cigarettes (e-cigarettes) may be used as an HPHC-reduced alternative to smoking tobacco. In an e-cigarette, a mechanism reduces a liquid ("e-cigarette fluid," "e-fluid," "e-liquid," or "vaping fluid") into a smoke-like mixture of air and tiny droplets (an aerosol) which material is then inhaled by the user. Any active constituents in the vaping fluid may then be absorbed by the lungs like real cigarette smoke. Because e-cigarettes do not produce smoke, other terms have been developed to describe using the devices (e.g., "vaping.") The most common type of e-cigarette has a heating element causing the vaporization of the e-fluid to create an aerosol. Other types of e-cigarettes may use mechanical production of the aerosol (e.g., a piezoelectric diaphragm vibrating at ultrasonic speeds to directly form an aerosol from the e-fluid, similar to a misting humidifier).

Sugar esters in a tobacco leaf are key components for tobacco aroma. They are generally stable at ambient conditions. When heat is applied, they undergo thermolysis and release carboxylic acids and reduced sugars, which may be useful as raw materials for, e.g., the food industry, flavorant production, as well as the tobacco industry in particular as an additive for novel tobacco products.

Typically, some processes may attempt to manufacture tobacco material that enriches sugar esters (or other compounds), which is focusing on raising the concentration of such compounds during the drying of the tobacco leaf. Generally, some sugar ester synthesis processes may require enzyme catalysis. Such enzyme catalysis processes may be sensitive to environmental parameters. Without careful control of reaction conditions, the enzyme may be impacted and lose its activity. Such reactions typically have lower than, e.g., 80% purity.

As will be discussed in greater detail below, the present disclosure may include a scalable process for the synthesis of, e.g., sugar esters, which are naturally found in tobacco plants. This process may produce targeted sugar esters with high purity, which may be directly used in the downstream production of materials for use in novel tobacco products or otherwise.

In some implementations, as will also be discussed in greater detail below, the present disclosure may provide one or more example synthesis processes that may not require catalysts and are easy to control and execute by those skilled in the organic chemistry art. In some implementations, the example process(es) are generalizable to various types of sugars and carboxylic (or fatty) acids with C-chain length ranging from, e.g., C2-C22. In some implementations, the process(es) may provide high purity products (e.g., >90%) at a yield that is higher than existing processes.

As such, some example and non-limiting advantages of the present disclosure may include: (1) A straightforward process without the need of extreme temperature, pressure conditions, or catalysts using common (or uncommon) organic solvents during the reaction(s); (2) two simplified reaction steps, which may use overage carboxylic acid anhydride to produce intermediate pentaester in the first step (esterification), and basic reagent in the second step to selectively reduce one acidic functional group from the sugar structure to produce tetraester (de-esterification). Such a process eliminates the need of attaching acidic groups to the sugar structure stepwise; (3) Easily scalable to fulfill the needs of downstream production; and (4) Higher purity.

Referring also at least to some of the example implementations of FIGS. 1-10, as will be discussed below, a process for making a glucose tetraester may include but is not limited to reacting 900 glucose with a carboxylic acid to create a glucose pentaester. The glucose pentaester was reacted 902 with a basic reagent to create a glucose tetraester.

Referring also at least to some of the example implementations of FIGS. 1-10, as will be discussed below, a process for making a glucose tetraester may include but is not limited to reacting 1000 glucose with a carboxylic acid anhydride in the presence of 4-dimethylaminopyridine to create a glucose pentaester product. The glucose pentaester reaction product was separated 1002. The glucose pentaester reaction product was reacted 1004 with a basic reagent, wherein the reaction steps may take place at a temperature of about 0° C. to about 60° C. and about ambient pressure, wherein the ratio of the carboxylic acid to the glucose was from about 5:1 to about 50:1, and wherein the ratio of the glucose pentaester to the basic reagent was from about 1:50 to about 1:150.

Referring also at least to some of the example implementations of FIGS. 1-10, as will be discussed below, in some implementations, the reactions are not enzyme catalyzed. In some implementations, the reaction of glucose with the carboxylic acid is performed at a temperature of about 0° C. to about 60° C. In some implementations, the reaction of the glucose pentaester with the basic reagent is performed at a temperature of about 0° C. to about 60° C. In some implementations, the chemical purity is about 95%. In some implementations, the glucose pentaester product includes one of glucose pentamethylvalerate, glucose pentaproprionate, and glucose pentavalerate. In some implementations, the glucose tetraester is glucose tetramethylvalerate. In some implementations, the glucose tetraester is glucose tetrapropionate. In some implementations, the glucose tetraester is glucose tetravalerate. In some implementations, the glucose is α-D-glucose. The reaction of glucose with the carboxylic acid takes place in the presence of 4-dimethylaminopyridine. In some implementations, the reaction of glucose with the carboxlyic acid is performed at about ambient pressure. In some implementations, the basic reagent is ammonia. In some implementations, a ratio of the carboxylic acid to glucose is from about 5:1 to about 50:1. In some implementations, a ratio of the carboxylic acid to glucose is from about 10:1 to about 40:1. In some implementations, a ratio of the glucose pentaester to the basic reagent is from about 1:50 to about 1:150, or 1:50 to about 1:100.

Figure 1:
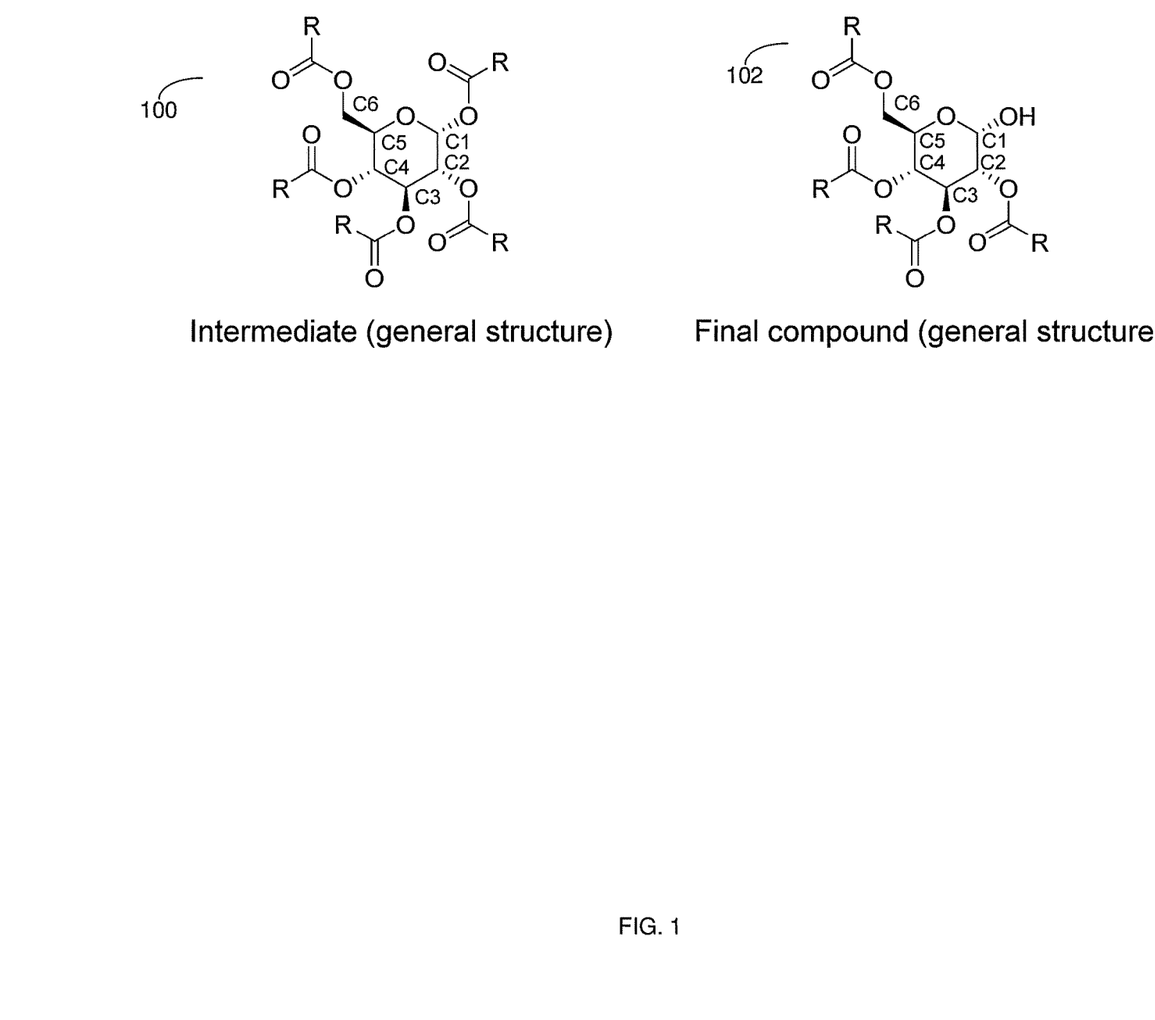
FIG. 1 is an example diagrammatic view of a general intermediate structure and a general final compound structure according to one or more example implementations of the disclosure.

Generally, and referring at least to the example implementation of FIG. 1, the synthesis of sugar esters is a 2-step reaction, shown with a general intermediate structure 100 and a general final compound structure 102. H-NMR Characteristic peaks (estimates)—Solvent: $CDCl_3$ Intermediate (General Structure)
C1-H: ~6.4 ppm
C5-H: ~5.5 ppm
C2-H & C3-H: ~5.2 ppm
C4-H: ~4.3 ppm
C6-H: ~4.1 ppm Final Compound (General Structure)
C1α-H & C4α-H: ~5.5 ppm
C3α-H & C4β-H: ~5.4 ppm
C2α-H: ~5.2 ppm
C2β-H & C3β-H: ~5.0 ppm
C1β-H: ~4.7 ppm
C5α-H: ~4.5 ppm
C6α-H & C6β-H: ~4.2 ppm
C5β-H: ~4.0 ppm In some implementations, as will be discussed further below, the disclosed process may use simple sugars (e.g., monosaccharides or disaccharides) and carboxylic acids as reactants, and common organic solvents, for example $CH_2Cl_2$ or ethyl acetate. It will be appreciated that other solvents that may be used may include, e.g.: DMF, $H_2O$, MeOH, $CHCl_3$ or EtOH. Triethyl amine or pyridine are not common solvents. In some implementations, the reactants were stirred at or around room temperature or 0° C. under a nitrogen atmosphere and later concentrated and partitioned using $KHSO_4$ and EtOAc or other inorganic/organic combination, for example, $KH_2PO_4$/EtOAc (1:1). In some implementations, the produced intermediate was further washed saturated sodium salt solutions (for example NaCl, or $NaHCO_3$, or a combination of the two). In some implementations, the extracted intermediate was dried with, e.g., MgSO$_4$, filtered, and chromatographed. In some implementations, a silica gel and EtOAc/Hexanes mixture was used for chromatography. The structure of the intermediate was confirmed by MS and H NMR. It will be appreciated that either process steps of the 2-step reaction discussed throughout were carried out without an enzyme catalyst, and at or about atmospheric pressure, for example, at about 101.325 kPa.

In some implementations, as may be shown further below, once the structure of the intermediate is confirmed, the intermediate was stirred at, e.g., 0° C. under nitrogen blanket in a common organic solvent mixture (for example, ammonia in THF/MeOH solution, or in DMF). In some implementations, the total amount of the solvent mixture was added stepwise using stirring. After the intermediate is stirred for at least 6 hours, the sample was concentrated and partitioned between, e.g., saturated KH$_2$PO$_4$ and EtOAc. In some implementations, the organic extract was washed with, e.g., saturated NaCl solution and dried by, e.g., MgSO$_4$, filtered, concentrated and chromatographed. In some implementations, silica gel and EtOAc/Hexanes mixture was used for chromatography. In some implementations, MS and NMR was used to confirm the sugar ester structure.

Generally, as shown in the example implementation of FIG. 1, there are examples and non-limiting structures and NMR peaks for intermediates and final target compounds. General Experimental Procedures: All reactions were performed in air-dried glassware fitted with rubber septa under a positive pressure of nitrogen, unless otherwise noted, although other similar techniques may be used. Organic solutions were concentrated by rotary evaporation (pump vacuum, ~30-200 mbar) at ~20-60° C., unless otherwise noted, although other similar techniques may be used. Flash column chromatography was performed using Silicycle UltraPure silica gel (230-400 mesh).

Example 1

Figure 2:
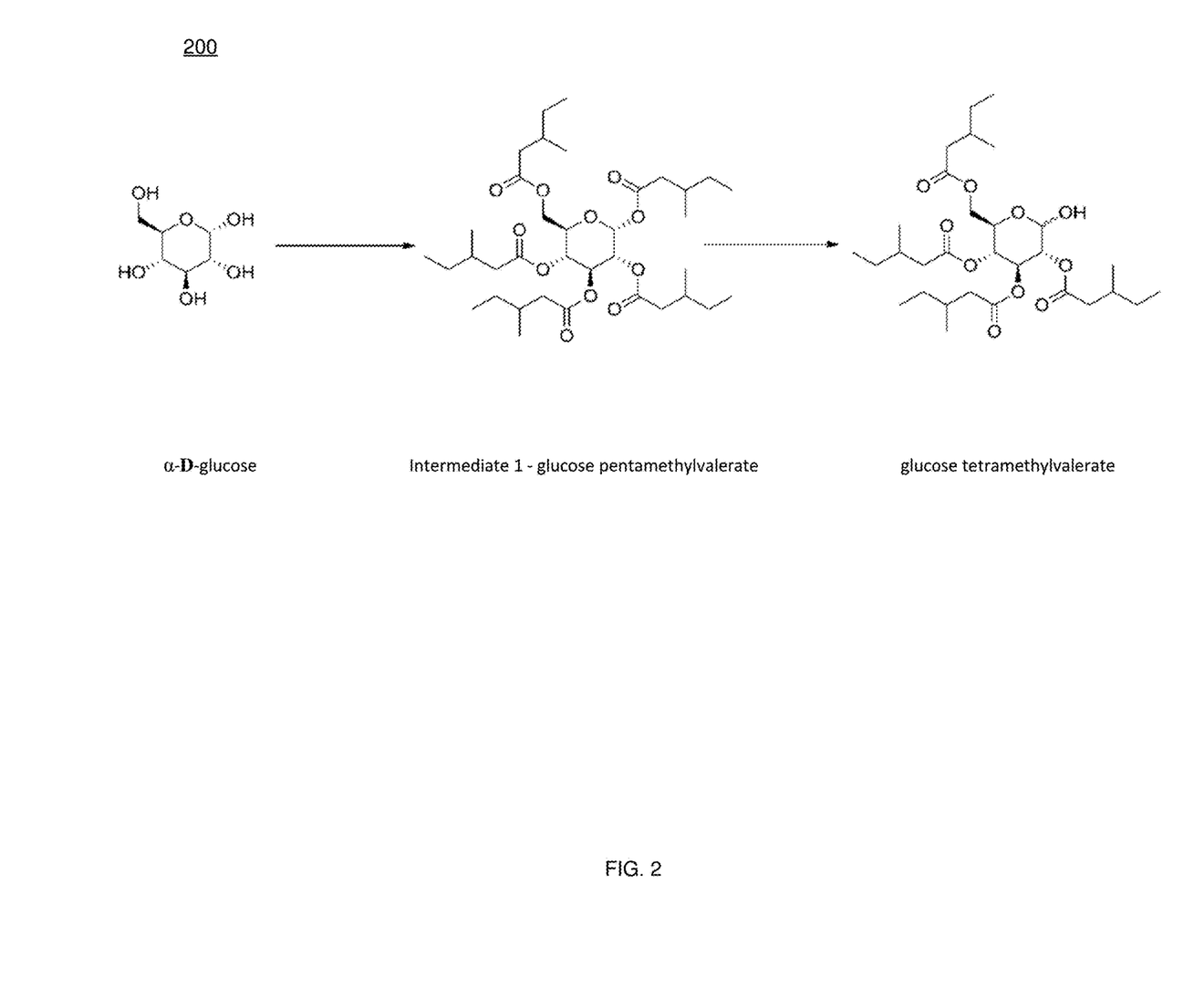
FIG. 2 is an example diagrammatic view of a 2-step reaction for making a glucose tetraester according to one or more example implementations of the disclosure.

Referring at least to the example implementation of FIG. 2, an example diagrammatic view of a 2-step reaction 200 for making a glucose tetraester according to one or more example implementations of the disclosure is shown.

Compound name: (3R,4S,5R,6R)-2-hydroxy-6-(((3-methylpentanoyl)oxy)methyl)tetrahydro-2H-pyran-3,4,5-triyl tris (3-methylpentanoate) or glucose tetramethylvalerate Molecular Formula: C$_{30}$H$_{52}$O$_{10}$
Molecular Weight: 572.74
Example and non-limiting preparation procedure:
To a stirring solution at ~0° C. under N$_2$ of 3-methylvaleric acid (2.0 mL, 16.0 mmol) and DMF (~4 drops) in CH$_2$Cl$_2$ (50 mL) was added dropwise oxalyl chloride (2.1 mL, 24.1 mmol). The reaction will release H-bearing process side products. N$_2$ blanketing is to ensure no oxidation side reaction from Oxygen in the ambient air. The sample was allowed to warm to room temperature overnight. The sample was concentrated, redissolved into CH$_2$Cl$_2$ (~10 mL) then was added dropwise to a stirring room temperature solution of α-D-glucose (0.30 g, 1.66 mmol) and 4-dimethylaminopyridine (20 mg, 0.16 mmol) in pyridine (10 mL). While α-D-glucose is disclosed as the glucose being used, it will be appreciated that other types of glucose may also be used. After, e.g., 16 hours at room temperature under N$_2$, the sample was concentrated then partitioned between 1 M KHSO$_4$ solution and EtOAc (50 mL of each). The organic extracted was washed with sat. NaHCO$_3$ and sat. NaCl solutions (50 mL of each), dried (MgSO$_4$), filtered, concentrated and chromatographed (silica gel, 10% EtOAc in hexanes) to give glucose pentamethylvalerate, (0.97 g, 87%) as a light yellow liquid. MS (ES+) m/z 693 (M+23, 75%) and 167 (100%). HNMR (500 MHz, CDCl$_3$) is consistent with the structure. It will be appreciated that solvent CH$_2$Cl$_2$ has a low boiling point, thus the initial step was conducted at ~0° C. to ensure minimal evaporation of CH$_2$Cl$_2$ and avoid concentrating the reactant. Once the reaction and solvent were thoroughly mixed, ambient condition was used for easiness of operation. Temperature does not have to be carefully controlled, so the sample was simply removed from ~0° C. ice-water bath. As such, a subrange that may be used can be ambient room temperature (e.g., 10-40° C.), and preferably controlled room temperature (e.g., 20-25° C., with excursions 15-30° C.).

To stirring solution at ~0° C. under N$_2$ of glucose pentamethylvalerate (0.97 g, 1.44 mmol) in THF (14 mL) was added dropwise ammonia, ca. 7 N solution in MeOH (10 mL, 70 mmol). After 2 hours and then again after 4 hours more ammonia, ca. 7 N solution in MeOH (10 mL, 70 mmol) was added. Total amount of ammonia, ca. 7 N solution in MeOH added was 3×10 mL (30 mL, 210 mmol). After 6 h, TLC (SiO$_2$, 10% EtOAc in hexanes) may still show SM present. The sample was allowed to warm to room temperature overnight, concentrated then partitioned between sat. KH$_2$PO$_4$ solution and EtOAc (50 mL of each). The organic extract was washed with sat. NaCl solution (50 mL), dried (MgSO$_4$), filtered, concentrated and chromatographed (silica gel, 30% EtOAc in hexanes) to give (3R,4S,5R,6R)-2-hydroxy-6-(((3-methylpentanoyl)oxy)methyl)tetrahydro-2H-pyran-3,4,5-triyl tris(3-methylpentanoate) (0.32 g, 39%) as light yellow oil. MS (APCI) m/z 555 (M-17, 41%) and 109 (100%). HNMR (500 MHz, CDCl$_3$) is consistent with the structure.

Example 2

Figure 3:
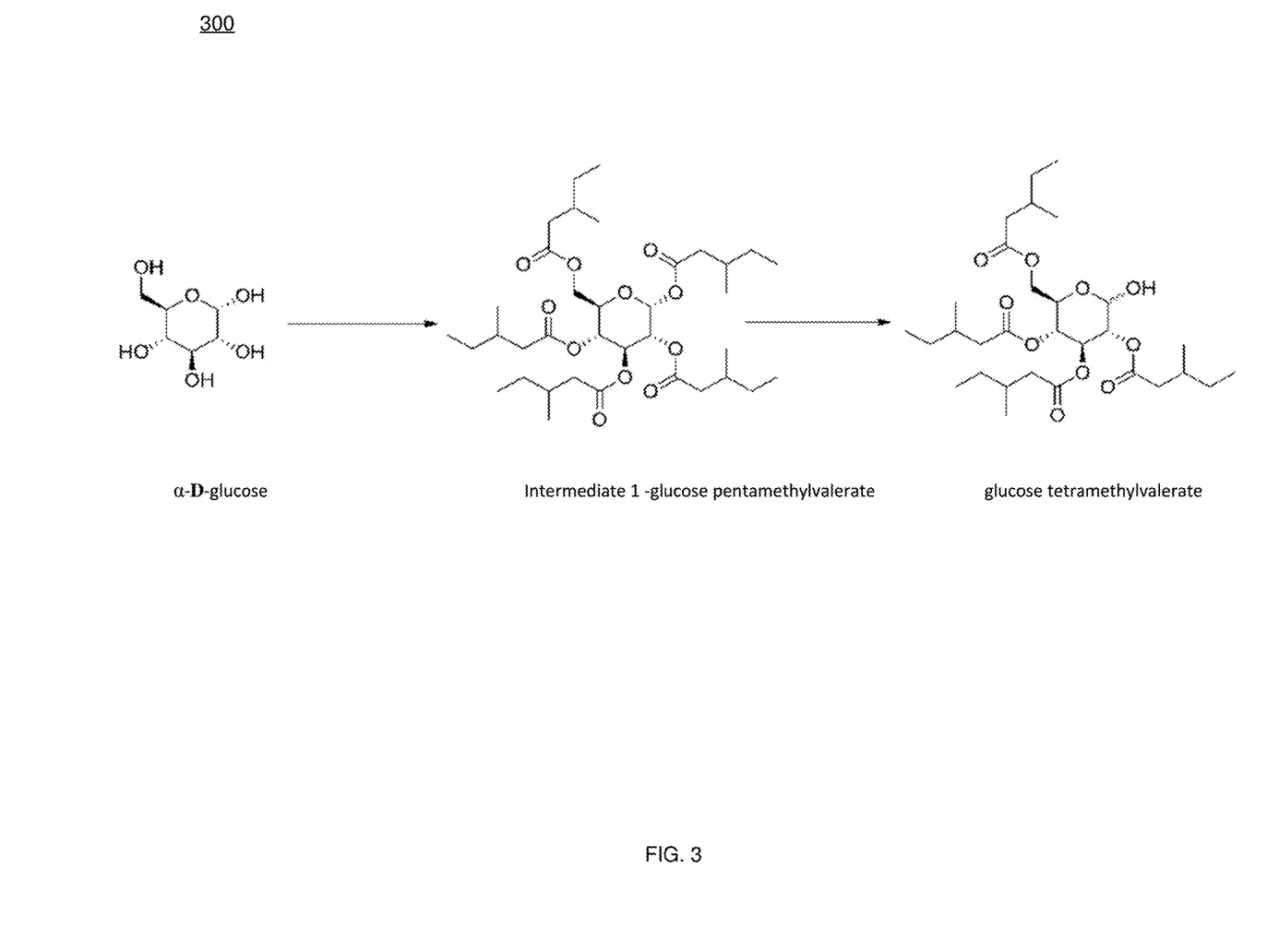
FIG. 3 is an example diagrammatic view of a 2-step reaction for making a glucose tetraester according to one or more example implementations of the disclosure.

Referring at least to the example implementation of FIG. 3, an example diagrammatic view of a 2-step reaction 300 for making a glucose tetraester according to one or more example implementations of the disclosure is shown. This is the same compound as in example 1, but larger scale, different solvent/reactants ratios and different yield. The yield is based on the starting materials for the specific experiment (e.g., glucose pentamethylvalerate). The yield is calculated as follows: moles of the product/moles of the starting material×100. To convert grams to moles, divide the amount in grams by the molecular weight.

Compound name: (3R,4S,5R,6R)-2-hydroxy-6-(((3-methylpentanoyl)oxy)methyl)tetrahydro-2H-pyran-3,4,5-triyl tris(3-methylpentanoate) or glucose tetramethylvalerate Molecular Formula: C$_{30}$H$_{52}$O$_{10}$
Molecular Weight: 572.74
Example and non-limiting preparation procedure:
To a stirring solution at ~0° C. under N$_2$ of 3-methylvaleric acid (51.60 g, 444.00 mmol) and DMF (~40 drops) in CH$_2$Cl$_2$ (250 mL) was slowly added oxalyl chloride (19.3 mL, 222.00 mmol). The sample was allowed to warm to room temperature overnight. The sample was concentrated and slowly added to a stirring room temperature solution of α-D-glucose (2.00 g, 11.10 mmol) and 4-dimethylaminopyridine (0.14 g, 1.11 mmol) in pyridine (50 mL). After 16 hours at room temperature under N$_2$, the sample was concentrated then partitioned between 1 M KHSO$_4$ solution and EtOAc (100 mL of each). The organic extracted was washed several times with sat. NaHCO$_3$ solution (50 mL) and once with sat. NaCl solution (100 mL), dried (Na$_2$SO$_4$), filtered, concentrated and chromatographed (silica gel, 10% EtOAc in hexanes) to give glucose pentamethylvalerate (4.84 g, 7.21 mmol, 65.0%) as light yellow oil.

MS(ESI): m/z 693 (M+Na)+

To a stirring solution at 0° C. under $N_2$ of glucose pentamethylvalerate (4.84 g, 7.21 mmol) in THF (75 mL) was slowly added ammonia, ca. 7 N solution in MeOH (20 mL, 140 mmol). After 2 hours and then again after 4 hours more ammonia, ca. 7 N solution in MeOH (20 mL, 140 mmol) was added. Total amount of ammonia, ca. 7 N solution in MeOH added was 3×20 mL (60 mL, 420 mmol). After 6 hours, the sample was removed from the ice-bath and the reaction mixture was allowed to stir for 18 additional hours. The reaction mixture was concentrated then partitioned between sat. $KH_2PO_4$ solution and EtOAc (100 mL of each). The organic extract was washed with sat. NaCl solution (100 mL), dried ($Na_2SO_4$), filtered, concentrated and chromatographed (silica gel, 30% EtOAc in hexanes) to give glucose tetramethylvalerate (2.60 g, 4.53 mmol, 62.8%) as a light yellow oil.

MS(ESI): m/z 595 (M+Na)$^+$

Example 3

Figure 4:
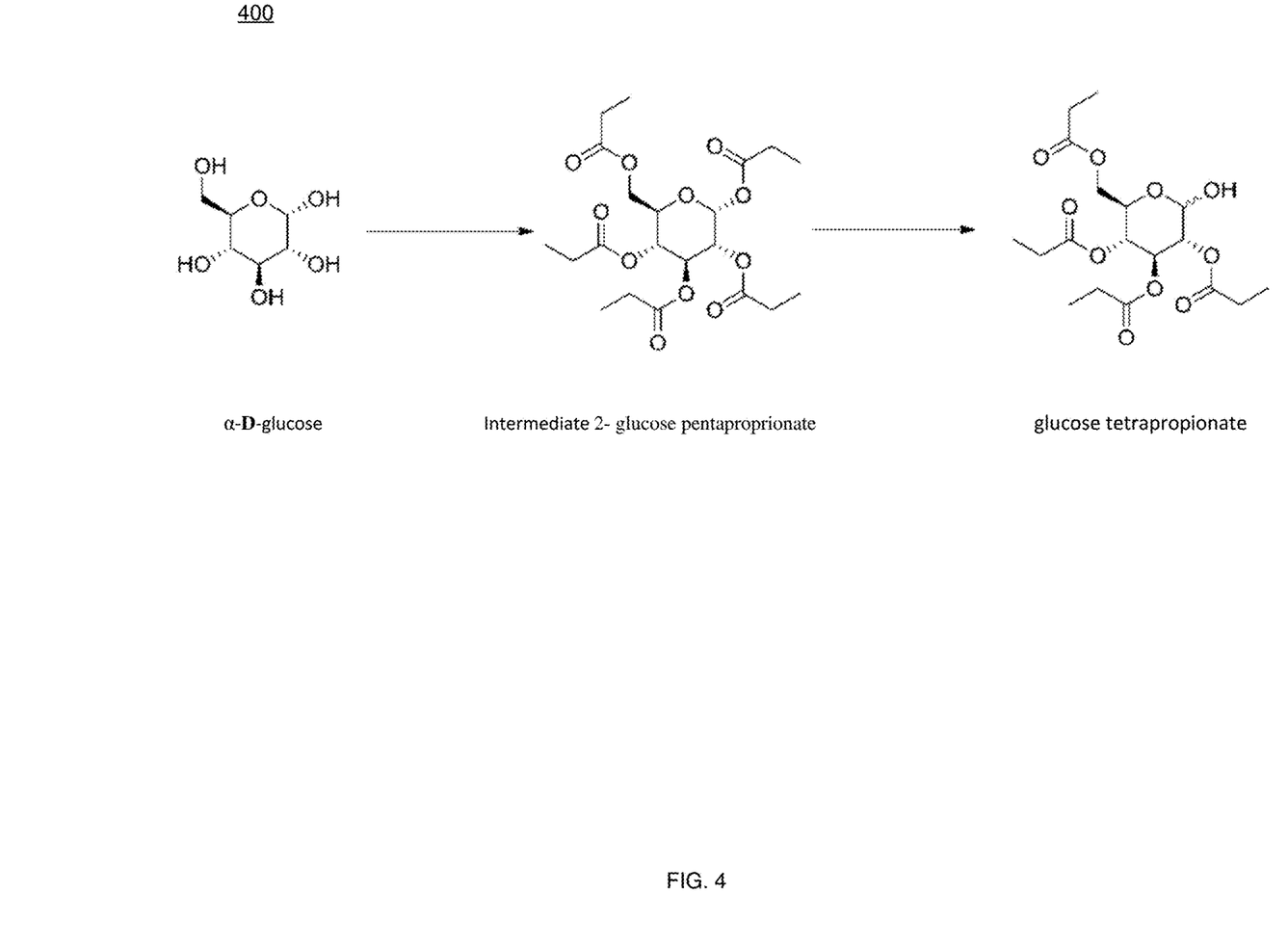
FIG. 4 is an example diagrammatic view of a 2-step reaction for making a glucose tetraester according to one or more example implementations of the disclosure.

Referring at least to the example implementation of FIG. 4, an example diagrammatic view of a 2-step reaction 400 for making a glucose tetraester according to one or more example implementations of the disclosure is shown.

Compound name: (3R,4S,5R,6R)-2-hydroxy-6-((propionyloxy)methyl)tetrahydro-2H-pyran-3,4,5-triyl tripropionate or glucose tetrapropionate Molecular Formula: $C_{18}H_{28}O_{10}$ Molecular Weight: 404.42

Example and non-limiting preparation procedure:

To a stirring solution at room temperature under $N_2$ of α-D-glucose (1.00 g, 5.55 mmol) and 4-dimethylaminopyridine (0.07 g, 0.57 mmol) in pyridine (15 mL) was added dropwise propionic anhydride (7.1 mL, 55.5 mmol). After 16 hours at room temperature under $N_2$, the sample was concentrated then partitioned between 1 M $KHSO_4$ solution and EtOAc (50 mL of each). The organic extracted was washed with sat. NaCl solution (50 mL), dried ($MgSO_4$), filtered, concentrated and chromatographed (silica gel, 20% EtOAc in hexanes) to give glucose pentaproprionate, (2.55 g, ~100%) as light yellow oil. MS (ES+) m/z 483 (M+1, 100%). H-NMR (500 MHz, $CDCl_3$) is consistent with the structure.

To stirring solution at ~0° C. under $N_2$ of glucose pentaproprionate (2.02 g, 4.38 mmol) in THF (60 mL) was added dropwise ammonia, ca. 7 N solution in MeOH (14 mL, 98 mmol). After 2 hours and then again after 4 hours more ammonia, ca. 7 N solution in MeOH (14 mL, 98 mmol) was added. Total amount of ammonia, ca. 7 N solution in MeOH added was 3×14 mL (42 mL, 294 mmol). After 6 hours, the sample was removed from the ice-bath, concentrated then partitioned between sat. $KH_2PO_4$ solution and EtOAc (100 mL of each). The organic extracted was washed with sat. NaCl solution (100 mL), dried ($MgSO_4$), filtered, concentrated and chromatographed (silica gel, 50% EtOAc in hexanes) to give (3R,4S,5R,6R)-2-hydroxy-6-((propionyloxy)methyl)tetrahydro-2H-pyran-3,4,5-triyl tripropionate (1.12 g, 64%) as white to off-white solid. MS (ES+) m/z 427 (M+23, 21%). H-NMR (500 MHz, $CDCl_3$) is consistent with the structure.

Example 4

Figure 5:
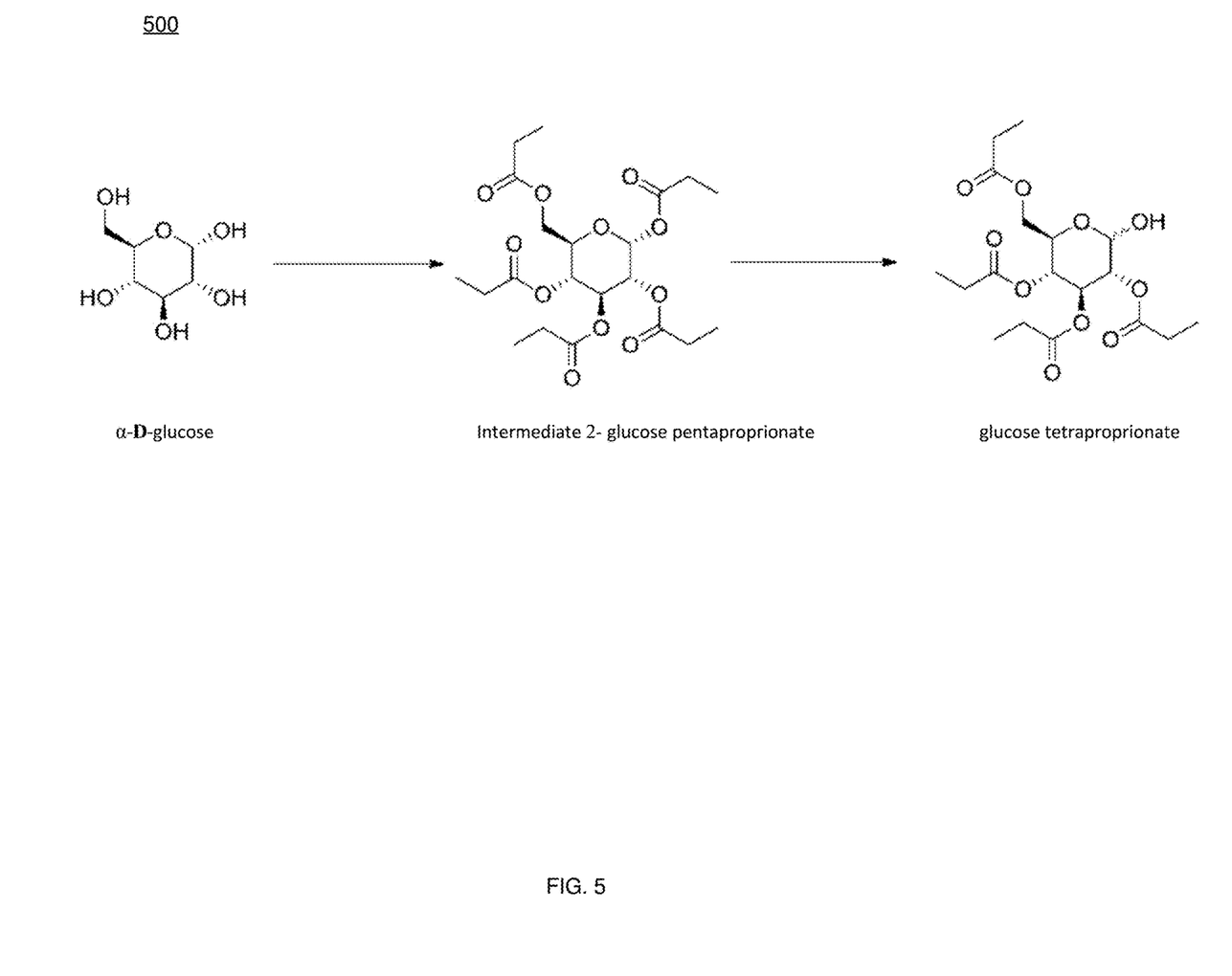
FIG. 5 is an example diagrammatic view of a 2-step reaction for making a glucose tetraester according to one or more example implementations of the disclosure.

Referring at least to the example implementation of FIG. 5, an example diagrammatic view of a 2-step reaction 500 for making a glucose tetraester according to one or more example implementations of the disclosure is shown. This is the same compound as in example 3, but on different scale, with different solvent/reactant ratios etc.

Compound name: (3R,4S,5R,6R)-2-hydroxy-6-((propionyloxy)methyl)tetrahydro-2H-pyran-3,4,5-triyl tripropionate or glucose tetrapropionate Molecular Formula: $C_{18}H_{28}O_{10}$ Molecular Weight: 404.42

Example and non-limiting preparation procedure:

To a stirring solution at room temperature under $N_2$ of α-D-glucose (4.00 g, 22.20 mmol) and 4-dimethylaminopyridine (0.27 g, 2.22 mmol) in pyridine (60 mL) was slowly added propionic anhydride (28.89 g, 222.0 mmol). After 16 hours at room temperature under $N_2$, the sample was concentrated then partitioned between 1 M $KHSO_4$ solution and EtOAc (100 mL of each). The organic extracted was washed several times with sat. $NaHCO_3$ solution (50 mL) and once with sat. NaCl solution (100 mL), dried ($Na_2SO_4$), filtered, concentrated and chromatographed (silica gel, 20% EtOAc in hexanes) to give glucose pentaproprioante (10.00 g, 21.72 mmol, 97.8%) as light yellow oil.

MS(ESI): m/z 483 (M+Na)$^+$

To a stirring solution at 0° C. under $N_2$ of glucose pentaproprionate (10.00 g, 21.72 mmol) in THF (125 mL) was slowly added ammonia, ca. 7 N solution in MeOH (25 mL, 175 mmol). After 2 hours and then again after 4 hours more ammonia, ca. 7 N solution in MeOH (25 mL, 175 mmol) was added. Total amount of ammonia, ca. 7 N solution in MeOH added was 3×25 mL (75 mL, 525 mmol). After 6 hours, the sample was removed from the ice-bath, concentrated then partitioned between sat. $KH_2PO_4$ solution and EtOAc (100 mL of each). The organic extracted was washed with sat. NaCl solution (100 mL), dried ($Na_2SO_4$), filtered, concentrated and chromatographed (silica gel, 50% EtOAc in hexanes) to give glucose tetraproprionate (6.5 g, 16.07 mmol, 74%) as a white solid.

MS(ESI): m/z 427 (M+Na)$^+$

Figure 6:
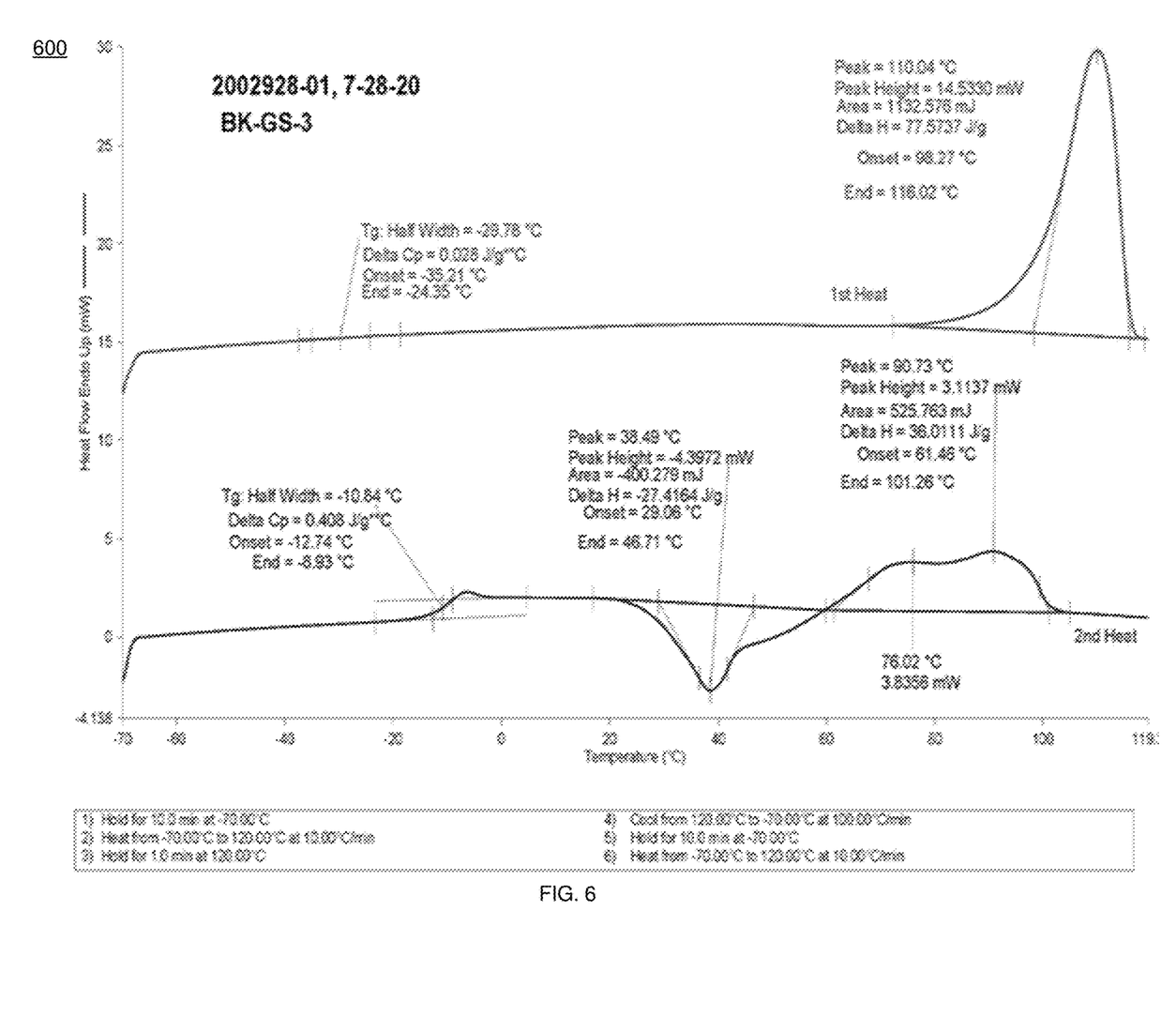
FIG. 6 is an example solid state thermal characterization of glucose tetraproprionate according to one or more example implementations of the disclosure.

As shown in the example chart 600 of the example implementation of FIG. 6, a solid state thermal characterization of glucose tetraproprionate was conducted and found that it exhibit a melting temperature onset at about 98° C. and peak at about 110° C. It also exhibit a cold crystalline temperature at about 38° C. when undergone a heat-cool cycle.

Example 5

Figure 7:
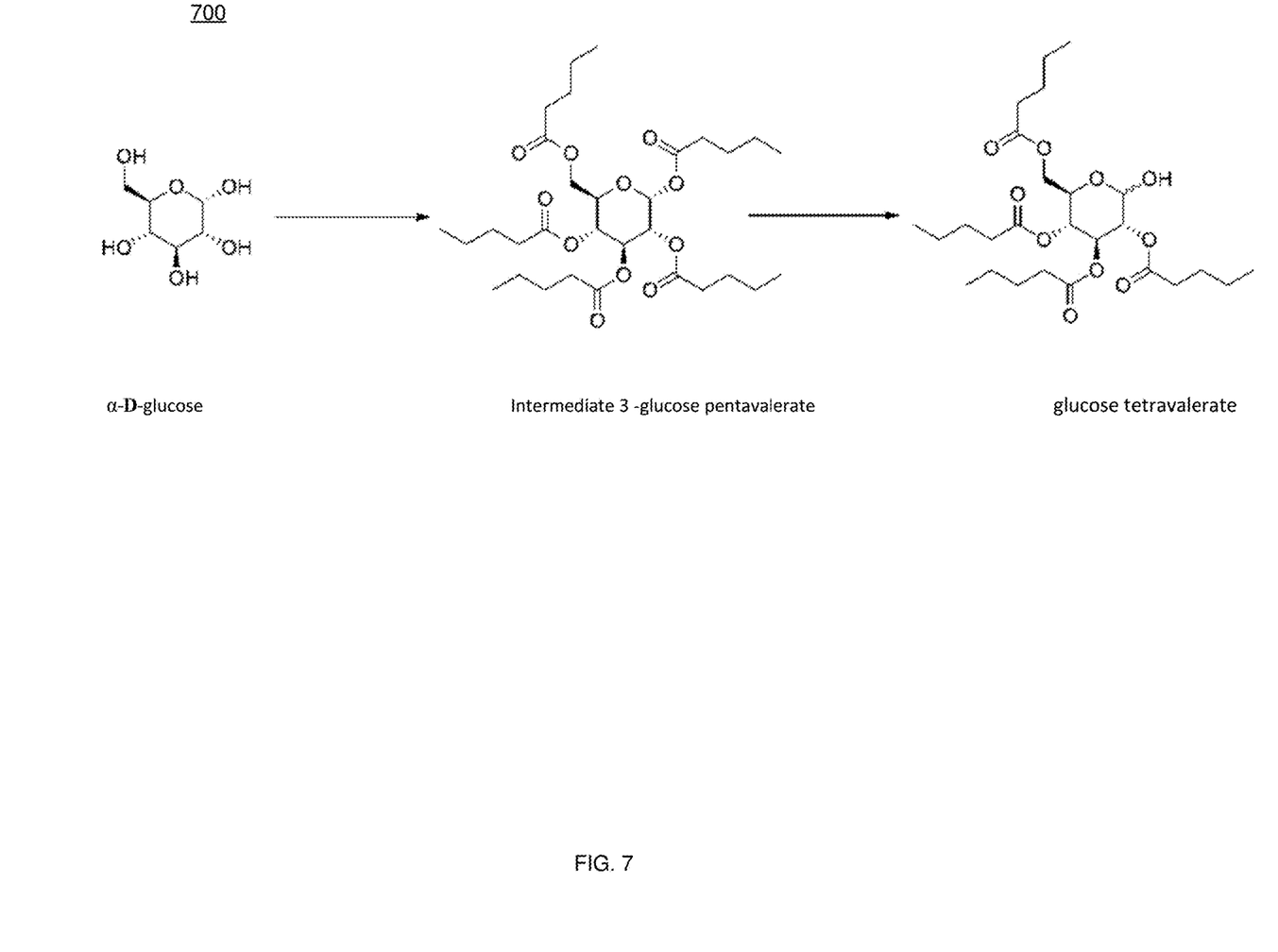
FIG. 7 is an example diagrammatic view of a 2-step reaction for making a glucose tetraester according to one or more example implementations of the disclosure.

Referring at least to the example implementation of FIG. 7, an example diagrammatic view of a 2-step reaction 700 for making a glucose tetraester according to one or more example implementations of the disclosure is shown.

Compound name: (3R,4S,5R,6R)-2-hydroxy-6-((pentanoyloxy)methyl)tetrahydro-2H-pyran-3,4,5-triyl tripentanoate or glucose tetravalerate Molecular Formula: $C_{26}H_{44}O_{10}$ Molecular Weight: 516.63

Example and non-limiting preparation procedure:

To a stirring solution at room temperature under $N_2$ of α-D-glucose (1.00 g, 5.55 mmol) and 4-dimethylaminopyridine (68 mg, 0.56 mmol) in pyridine (11 mL) was added dropwise valeric anhydride (11 mL, 56 mmol). After 16 hours at room temperature under $N_2$, the sample was concentrated then partitioned between 1 M $KHSO_4$ solution and EtOAc (50 mL of each). The organic extracted was washed with sat. NaCl solution (50 mL), dried ($MgSO_4$), filtered, concentrated and chromatographed (silica gel, 20% EtOAc in hexanes) to give glucose pentavalerate, (3.41 g, >100%) as light yellow liquid. MS (ES+) m/z 623 (M+23, 12%) and 317 (100%). HNMR (500 MHz, CDCl$_3$) is consistent with the structure.

To stirring solution at ~0° C. under N$_2$ of glucose pentavalerate (3.4 g) in THF (60 mL) was added dropwise ammonia, ca. 7 N solution in MeOH (10 mL, 70 mmol). After 2 hours and then again after 4 hours more ammonia, ca. 7 N solution in MeOH (10 mL, 70 mmol) was added. Total amount of ammonia, ca. 7 N solution in MeOH added was 3×10 mL (30 mL, 210 mmol). After 6 h, the sample was removed from the ice-bath, concentrated then partitioned between sat. KH$_2$PO$_4$ solution and EtOAc (50 mL of each). The organic extracted was washed with sat. NaCl solution (50 mL), dried (MgSO$_4$), filtered, concentrated and chromatographed (silica gel, 20% EtOAc in hexanes) to give (3R,4S,5R,6R)-2-hydroxy-6-((pentanoyloxy)methyl)tetrahydro-2H-pyran-3,4,5-triyl tripentanoate (1.10 g, 38%) as light yellow oil. MS (ES+) m/z 539 (M+23, 100%). HNMR (500 MHz, CDCl$_3$) is consistent with the structure.

Example 6

Figure 8:
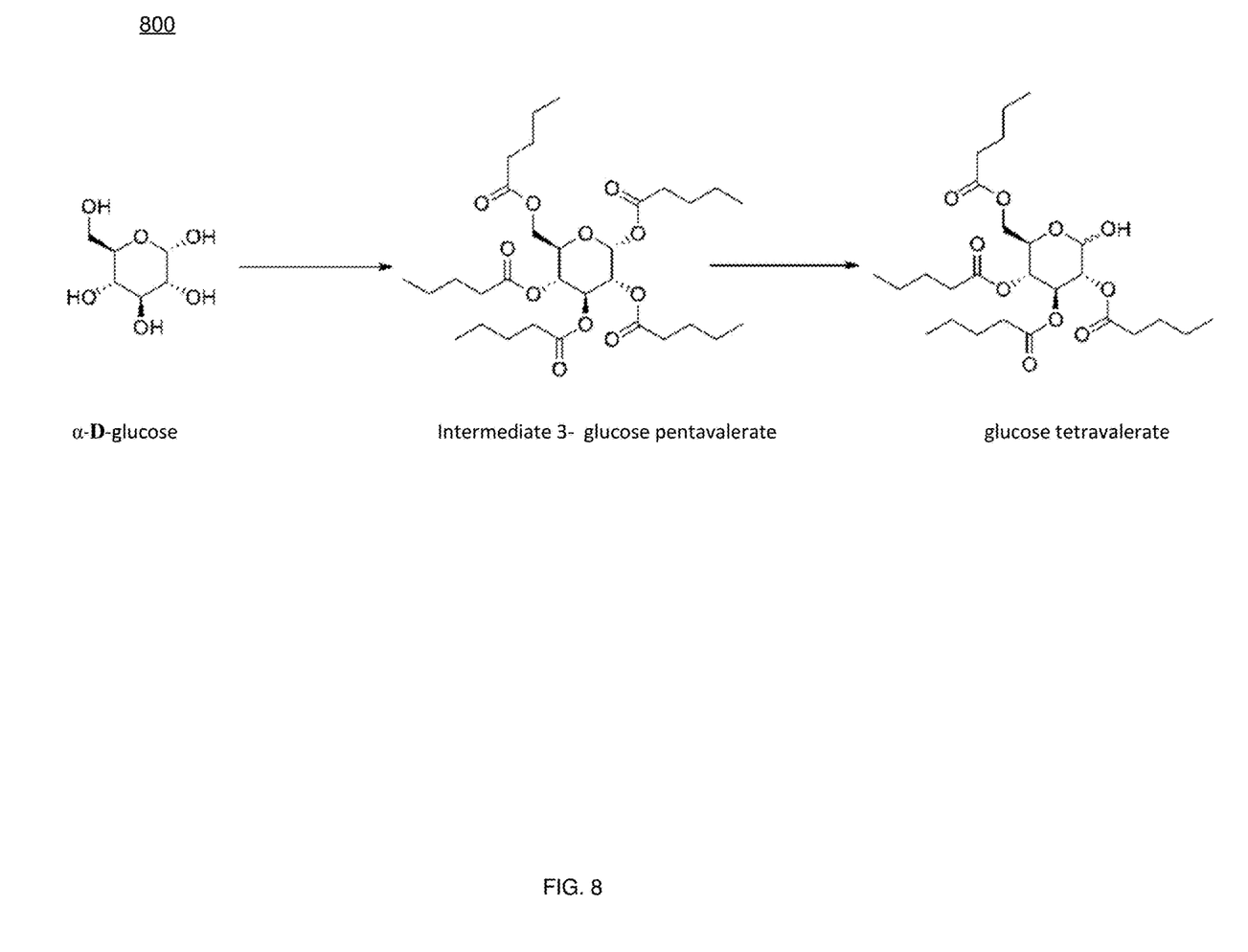
FIG. 8 is an example diagrammatic view of a 2-step reaction for making a glucose tetraester according to one or more example implementations of the disclosure.
Figure 9:
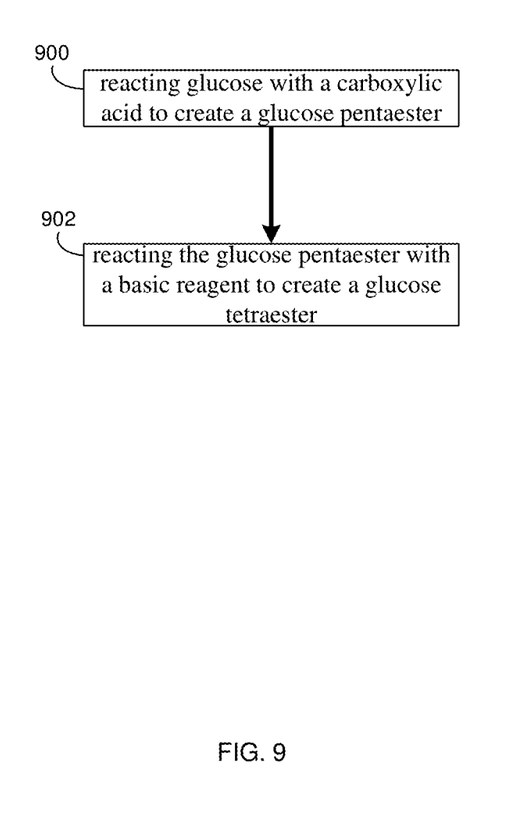
FIG. 9 is an example flowchart of a process for making a glucose tetraester according to one or more example implementations of the disclosure.
Figure 10:
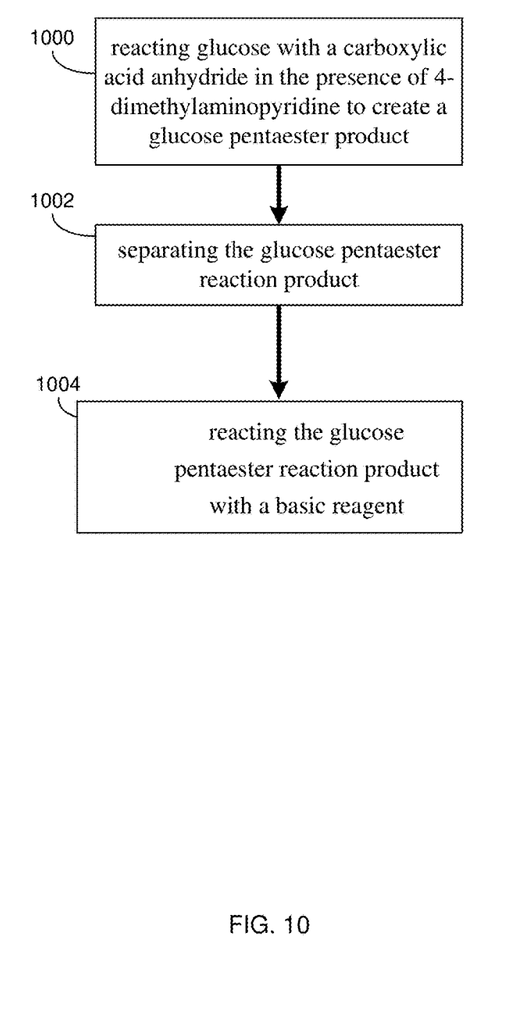
FIG. 10 is an example flowchart of a process for making a glucose tetraester according to one or more example implementations of the disclosure.

Referring at least to the example implementation of FIG. 8, an example diagrammatic view of a 2-step reaction 800 for making a glucose tetraester according to one or more example implementations of the disclosure is shown. This is the same compound as in example 5, but on different scale, with different solvent/reactant ratio.

Compound name: (3R,4S,5R,6R)-2-hydroxy-6-((pentanoyloxy)methyl)tetrahydro-2H-pyran-3,4,5-triyl tripentanoate or glucose tetravalerate Molecular Formula: C$_{26}$H$_{44}$O$_{10}$ Molecular Weight: 516.63

Example and non-limiting preparation procedure:

To a stirring solution at room temperature under N$_2$ of α-D-glucose (4.00 g, 22.20 mmol) and 4-dimethylaminopyridine (0.27 g, 2.22 mmol) in pyridine (60 mL) was slowly added valeric anhydride (41.35 g, 222.0 mmol). After 16 hours at room temperature under N$_2$, the sample was concentrated then partitioned between 1 M KHSO$_4$ solution and EtOAc (100 mL of each). The organic extracted was washed several times with sat. NaHCO$_3$ solution (50 mL) and once with sat. NaCl solution (100 mL), dried (Na$_2$SO$_4$), filtered, concentrated and chromatographed (silica gel, 20% EtOAc in hexanes) to give glucose pentavalerate (9.07 g, 15.10 mmol, 68.0%) as light yellow oil.

MS(ESI): m/z 623 (M+Na)$^+$

To a stirring solution at 0° C. under N$_2$ of glucose pentavalerate (9.07 g, 15.10 mmol) in THF (125 mL) was slowly added ammonia, ca. 7 N solution in MeOH (20 mL, 140 mmol). After 2 hours and then again after 4 hours more ammonia, ca. 7 N solution in MeOH (20 mL, 140 mmol) was added. Total amount of ammonia, ca. 7 N solution in MeOH added was 3×20 mL (60 mL, 420 mmol). After 6 hours, the sample was removed from the ice-bath, concentrated then partitioned between sat. KH$_2$PO$_4$ solution and EtOAc (100 mL of each). The organic extracted was washed with sat. NaCl solution (100 mL), dried (Na$_2$SO$_4$), filtered, concentrated and chromatographed (silica gel, 20% EtOAc in hexanes) to give glucose tetravalerate (5.5 g, 10.65 mmol, 70.5%) as a light yellow oil.

MS(ESI): m/z 539 (M+Na)$^+$

It will be appreciated that the procedural timing and amounts of the above-noted compounds may vary without departing from the scope of the disclosure in order to achieve the same or similar desired results. As such, the discussion of specific amounts of time and amounts of compounds (as well as the example compounds themselves) should be taken as example only.

In some implementations, the produced sugar ester was used as one of the key components in a nicotine e-liquid, in which after being vaporized, may stabilize nicotine in the vapor, enhance the nicotine transfer rate from the e-liquid, and may provide a natural tobacco like flavor.

In some implementations, the produced sugar ester was used in the production of process tobacco insert or tobacco sheet for heat-not-burn tobacco product as an ingredient that may enhance the nicotine transfer rate from the tobacco and may enhance the natural tobacco like flavor.

The thermal stability of all sugar tetraester compounds described in the examples were studied under different conditions: 1) as neat compound 2) with nicotine:compound 1:4 molar ratio 3) with nicotine:compound at 1:4 molar ratio in propylene glycol at a 3% nicotine concentration level. All experimental compounds or mixtures were heated using a metal heating block at 150° C., 200° C., 250° C. for 30 minutes respectively. The contents post-heating were either dissolved in MeOH or CDCl3 and analyzed by mass spec to observe any potential decomposition of the example sugar tetraesters.

The neat sugar tetraester compounds were found to be thermally stable up to 250° C. All sugar tetraester compounds decomposed when nicotine or nicotine/propylene glycol were present starting as low as 150° C. The rate of the decomposition is significantly affected by the presence of nicotine and nicotine/propylene glycol. The sugar tetraesters were nearly complete decomposed at or above 200° C.

The thermal behavior of the sugar tetraesters make them potentially key components in a nicotine e-cigarette products which are typically stored at room temperature but heated to 180-200° C. when being used.

While directly processing on tobacco material may be limited to its use on tobacco products (e.g., for use with an electronic vaporization device), it will be appreciated that the disclosed processes may provide a solution to isolate pure sugar esters which could be used in other industries, such as the food industry or the pharmaceutical industry. As such, while the present disclosure is discussed in terms of tobacco material for vaping, other organic materials and uses may also be included within the scope of the present disclosure.

The terminology used herein is for the purpose of describing particular implementations only and is not intended to be limiting of the disclosure. As used herein, the singular forms "a", "an" and "the" are intended to include the plural forms as well, unless the context clearly indicates otherwise. As used herein, the language "at least one of A, B, and C" (and the like) should be interpreted as covering only A, only B, only C, or any combination of the three, unless the context clearly indicates otherwise. It will be further understood that the terms "comprises" and/or "comprising," when used in this specification, specify the presence of stated features, integers, steps (including those noted in flowcharts and not necessarily in a particular order), operations, elements, and/or components, but do not preclude the presence or addition of one or more other features, integers, steps (including those noted in flowcharts and not necessarily in a particular order), operations, elements, components, and/or groups thereof.

The corresponding structures, materials, acts, and equivalents (e.g., of all means or step plus function elements) that may be in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications, variations, substitutions, and any combinations thereof will be apparent to those of ordinary skill in the art without departing from the scope and spirit of the disclosure. The implementation(s) were chosen and described in order to explain the principles of the disclosure and the practical application, and to enable others of ordinary skill in the art to understand the disclosure for various implementation(s) with various modifications and/or any combinations of implementation(s) as are suited to the particular use contemplated.

Having thus described the disclosure of the present application in detail and by reference to implementation(s) thereof, it will be apparent that modifications, variations, and any combinations of implementation(s) (including any modifications, variations, substitutions, and combinations thereof) are possible without departing from the scope of the disclosure defined in the appended claims.

What is claimed is:

1. A method for making a glucose tetraester, comprising:
   a. reacting glucose with a carboxylic acid to create a glucose pentaester, wherein the glucose pentaester includes one of glucose pentamethylvalerate, glucose pentaproprionate, and glucose pentavalerate; and
   b. reacting the glucose pentaester with a basic reagent to create a glucose tetraester.

2. The method of claim 1 wherein the reactions are not enzyme catalyzed.

3. The method of claim 1 wherein the reaction of glucose with the carboxylic acid is performed at a temperature of about 0° C. to about 60° C.

4. The method of claim 1 wherein the reaction of the glucose pentaester with the basic reagent is performed at a temperature of about 0° C. to about 60° C.

5. The method of claim 1 wherein the glucose tetraester is glucose tetramethylvalerate.

6. The method of claim 1 wherein the glucose tetraester is glucose tetrapropionate.

7. The method of claim 1 wherein the glucose tetraester is glucose tetravalerate.

8. The method of claim 1 wherein the glucose is α-D-glucose.

9. The method of claim 1 wherein the reaction of glucose with the carboxylic acid takes place in the presence of 4-dimethylaminopyridine.

10. The method of claim 1 wherein the reaction of glucose with the carboxylic acid is performed at about ambient pressure.

11. The method of claim 1 wherein the basic reagent is ammonia.

12. The method of claim 1 wherein a ratio of the carboxylic acid to glucose is from about 5:1 to about 50:1.

13. The method of claim 12 wherein a ratio of the carboxylic acid to glucose is from about 10:1 to about 40:1.

14. The method of claim 1 wherein a ratio of the glucose pentaester to the basic reagent is from about 1:50 to about 1:150.

15. A method for making a glucose tetraester, comprising:
   a. reacting glucose with a carboxylic acid anhydride in the presence of 4-dimethylaminopyridine to create a glucose pentaester product;
   b. separating the glucose pentaester reaction product;
   c. reacting the glucose pentaester reaction product with a basic reagent;
   wherein the reaction steps take place at a temperature of about 0° C. to about 60° C. and about ambient pressure;
   wherein the ratio of the carboxylic acid anhydride to the glucose is from about 5:1 to about 50:1; and
   wherein the ratio of the glucose pentaester to the basic reagent is from about 1:50 to about 1:150.

16. The method of claim 15 wherein the glucose tetraester is glucose tetramethylvalerate.

17. The method of claim 15 wherein the glucose tetraester is glucose tetrapropionate.

18. The method of claim 15 wherein the glucose tetraester is glucose tetravalerate.

19. The method of claim 15 wherein the basic reagent is ammonia.

20. The method of claim 15 wherein the glucose pentaester product includes one of glucose pentamethylvalerate, glucose pentaproprionate, and glucose pentavalerate.

* * * * *